(12) United States Patent
Floyd

(10) Patent No.: US 8,216,164 B2
(45) Date of Patent: Jul. 10, 2012

(54) ORTHOTIC DEVICE RESPONSIVE TO ATMOSPHERIC PRESSURE CHANGE AND METHOD

(76) Inventor: Alexander Floyd, Pottsville, AR (US)

( * ) Notice: Subject to any disclaimer, the term of this patent is extended or adjusted under 35 U.S.C. 154(b) by 286 days.

(21) Appl. No.: 12/755,457

(22) Filed: Apr. 7, 2010

(65) Prior Publication Data

US 2011/0251538 A1    Oct. 13, 2011

(51) Int. Cl.
*A61F 5/00* (2006.01)
(52) U.S. Cl. .................. 602/13; 602/5; 602/60
(58) Field of Classification Search .............. 602/5, 13, 602/23, 26, 60–64
See application file for complete search history.

(56) References Cited

U.S. PATENT DOCUMENTS

| | | | |
|---|---|---|---|
| 4,378,009 A | 3/1983 | Rowley et al. | |
| 5,197,461 A | 3/1993 | Petajan et al. | |
| 5,383,843 A | 1/1995 | Watson et al. | |
| 5,385,538 A | 1/1995 | Mann | |
| 5,407,421 A | 4/1995 | Goldsmith | |
| 5,558,627 A | 9/1996 | Singer et al. | |
| 5,641,322 A | 6/1997 | Silver et al. | |
| 5,643,185 A | 7/1997 | Watson et al. | |
| 6,511,449 B2 | 1/2003 | Burns et al. | |
| 2010/0312361 A1* | 12/2010 | Martin | 623/34 |
| 2011/0184532 A1* | 7/2011 | Tompkins | 623/34 |
| 2011/0213255 A1* | 9/2011 | Finburgh et al. | 600/490 |

* cited by examiner

*Primary Examiner* — Kim M Lewis
(74) *Attorney, Agent, or Firm* — Stan Baker

(57) ABSTRACT

An orthotic such as a knee, ankle, elbow or wrist brace is provided. The orthotic includes one or more compression devices that adjust the amount of compressive force applied to a body part based upon fluctuations in atmospheric pressure. One embodiment of the invention incorporates one or more inflatable air bladders connected to an air pump and an atmospheric pressure sensor. The brace places the inflatable air bladder proximate a joint where it can be inflated to provide compressive support for the joint. The invention also comprises a method for adjusting the compressive force applied to a body part based upon fluctuations in atmospheric pressure.

17 Claims, 5 Drawing Sheets

ORTHOTIC DEVICE RESPONSIVE TO ATMOSPHERIC PRESSURE CHANGE AND METHOD

FIELD OF THE INVENTION

The present invention pertains to orthotics which are devices, such as a brace or a splint, for supporting, immobilizing, or treating muscles, joints, and skeletal parts which are weak, injured, deformed, or ineffective.

BACKGROUND

The typical human body contains about 206 bones and approximately 640 muscles resulting in about 230 moveable and semi-movable joints. Anatomists generally define a joint as any instance where two or more bones connect. They are constructed to allow movement of the skeleton and/or support of the body. Joints are usually classified structurally (i.e., fibrous, cartilaginous, or synovial); functionally (i.e., synarthrothis, amphiarthrosis, or diarthrosis); and biomechanically (i.e., simple, compound, or complex).

Synovial joints (synonymous with "diarthrosis") are the joints most people commonly think of when they hear of someone having injured a joint. Synovial joints include, but are not limited to, the ankle, knee, hip, shoulder, elbow, and wrist. Synovial joints are extremely complex structures containing numerous parts. A typical synovial joint comprises at least two bones, tendons connecting muscle to bone, ligaments connecting bone to bone, cartilage to cushion bones, specialized cells to create synovial fluid, and specialized tissue to surround and protect the interior of the joint (the "joint capsule"). Other possible components (depending on the joint) include articular discs and meniscus. Each joint is also innervated in some manner.

Because synovial joints are so complex, any damage to a single component can lead to decreased functionality of that joint. For example, professional athletes commonly tear or completely rupture their anterior cruciate ligament (ACL) which is a piece of fibrous tissue in the knee joint that helps keep the ends of femur and the tibia in their proper position during movement. Catastrophic injuries such as motorcycle accidents can essentially rip a joint apart by rupturing multiple components (i.e., ligaments, tendons, joint capsule).

Fortunately, modern surgical procedures can repair or replace a torn ACL and even whole knees. However, even with the surgical miracles at our disposal, some sufferers of joint injury never fully recover from the damage and experience some form of pain, such as arthritic pain, for the rest of their lives. Some sufferers of joint injury also experience some permanent loss of function in the joint or limb and require orthopedic support for that joint for the rest of their life. Long term pain management techniques including acupuncture, non-steroidal anti-inflammatory medications, and/or controlled medications may be necessary in some instances.

Many injured individuals awaiting surgical intervention, or those that never fully recover from joint injury, use orthotic devices to reduce stress on the joint and/or provide additional structural support and/or reduce pain. The area of orthotics is filled with numerous devices designed to provide support and protection to all of the major joints (i.e., knee, elbow, ankle, etc.). The vast majority of these known devices provide at least some degree of support, protection, and/or pain relief to a user. However, none of the known devices address a variable that has been associated with increased joint pain—changes in atmospheric pressure (aka barometric pressure).

All readers probably know of at least one individual who claims that an arthritic or injured joint becomes painful "when a storm is approaching" or an older relative who predicts the weather based on how their knee feels. There is no shortage of anecdotal evidence that a drop in atmospheric pressure, such as the drop that often accompanies a storm system, is somehow related to an increase in joint pain.

Over the years, several scientific studies have attempted to better quantify the apparent relationship between joint pain and atmospheric pressure changes. One such study consisted of 16 patients with rheumatoid arthritis, 24 patients with osteoarthritis, 11 patients with inflammatory arthritis, and 11 patients with fibromyalgia joint pain. 25% the patients with rheumatoid arthritis, 83% of the patients of with osteoarthritis, 64% of the patients with inflammatory arthritis, and 77% of the patients with fibromyalgia reported sensitivity to weather changes. Guedj and Weinberger, "Effects of Weather Conditions on Rheumatic Patients", Annuals of Rheumatic Diseases, 1990; 49:158-159.

Although the cause and effect between decreased atmospheric pressure and increased joint pain is likely multi-factorial, it is thought that one potential cause is the expansion of the joint capsule which is innervated. If a joint is injured or arthritic, the tissue within and surrounding the joint may become inflamed (i.e., thickened, swollen, etc.). This increases pressure within the joint. Over time the body may become acclimated to the increased joint pressure during periods of normal or high atmospheric pressure. However, one theory for weather related joint pain is that as the atmospheric pressure decreases there is less pressure "outside" of the joint offsetting the pressure "within" the joint. The joint capsule then expands, stretching the tissue and stimulating pain receptors. Again, the above explanation is only a theory but people have reported a decrease in pain sensation when slight additional pressure is applied to an injured joint during times of low atmospheric pressure.

Accordingly, there is a need for an orthotic which addresses the relationship between changes in atmospheric pressure and the pain/discomfort experienced by those with joint pain.

OBJECT AND SUMMARY OF THE INVENTION

In view of the above, it is an object of the present invention, among others, to provide an orthotic that is capable of providing support and protection to a joint or body part.

It is another object of the present invention to provide an orthotic that improves upon known orthotics by addressing the relationship between changes in atmospheric pressure and the pain/discomfort experienced by those with joint pain.

Briefly, and in general terms using exemplary language to aid but not limit the discussion, the above objects are met by the present invention which is directed to both an apparatus and a method for altering a compressive force on a body part in response to a change in atmospheric pressure.

The apparatus according to the invention encompasses an orthotic that monitors atmospheric pressure and increases the compressive force exerted on a body part when the atmospheric pressure falls below a predetermined value. In most instances it is envisioned that the apparatus according to the invention will comprise a compression device such as an inflatable air bladder connected to an air pump and an atmospheric sensor.

Accordingly, the method according to the invention broadly includes the steps of monitoring the atmospheric pressure and increasing the compressive force placed upon a body part if the atmospheric pressure falls below a predetermined value. In one embodiment the method is accomplished by turning on an air pump if the atmospheric pressure falls below a predetermined value and increasing the amount of air in an air bladder that is placed proximate a body part.

BRIEF DESCRIPTION OF THE DRAWINGS

The foregoing and other objects and advantages of the invention and the manner in which the same are accomplished will become clearer based on the following detailed description taken in conjunction with the accompanying drawings in which.

DETAILED DESCRIPTION

The present invention will now be described more fully hereinafter with reference to the accompanying drawings, in which a preferred embodiment of the invention is shown. However, this invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

One embodiment of the invention is an orthotic which is a device, such as a brace or a splint, for supporting, immobilizing, or treating body parts, such as muscles, joints, and skeletal parts which are weak, injured, deformed, or ineffective. Perhaps the most easily recognized orthotic is the knee brace. For this reason, this detailed description will utilize the knee brace as an exemplary orthotic for ease of discussion. However, the invention as described herein is equally applicable to other types of orthotics such as elbow braces and the like. More specifically, those skilled in the art can readily adapt the invention for use in any orthotic that provides compression or support for a body part.

Turning now to the Figures, a basic embodiment of the invention is an orthotic that is responsive to changes in atmospheric pressure. Specifically, the orthotic's components monitor atmospheric pressure and when atmospheric pressure falls below a predetermined value, the orthotic device increases compressive force to a body part.

Figure 4:
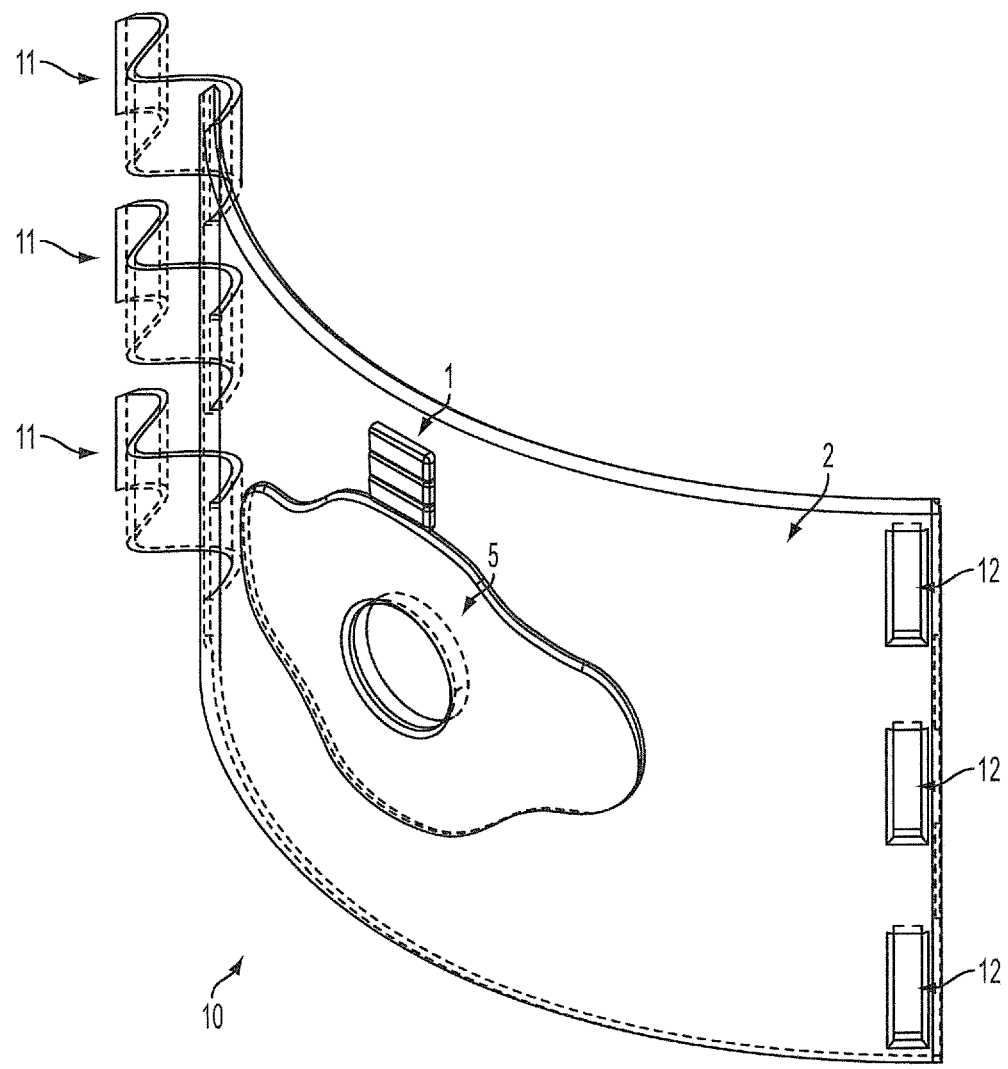
FIG. 4 is a representative drawing of a knee orthotic according to the invention.
Figure 5:
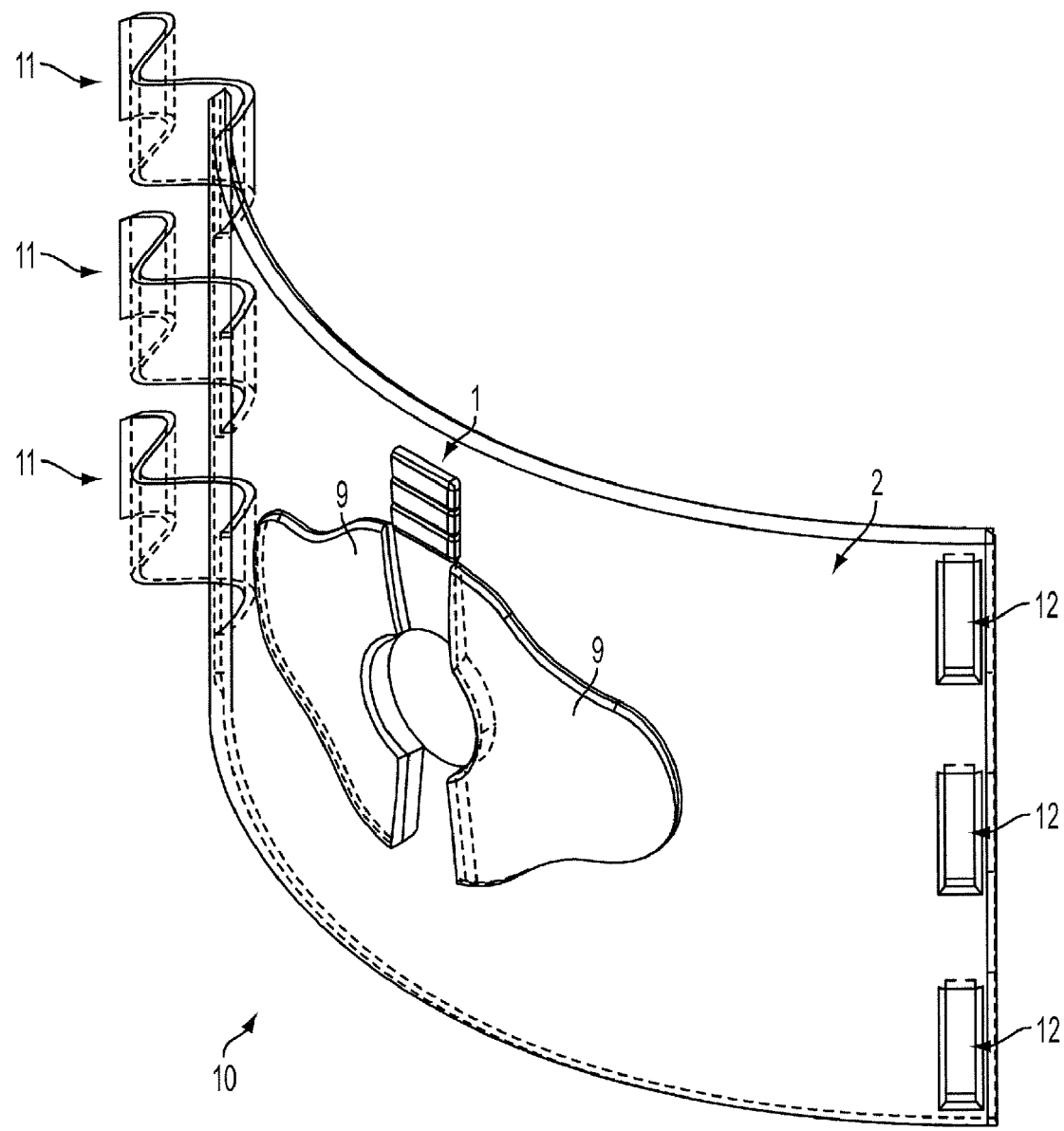
FIG. 5 is a representative drawing of a knee orthotic according to the invention.

In general terms, the apparatus according to the invention is an orthotic, generically represented as a knee brace in FIG. 4, that completely or partially envelops a body part (e.g., bones, muscles, joints, etc.). In most instances the body part enveloped by an orthotic is a joint, with ankles, knees, hips, shoulders, elbows, and wrists being among the most common joints supported by orthotics.

The knee brace 10 is a wrap around type which wraps around the knee and is connected by hook and loop straps 11 inserted into strap fasteners 12. In basic terms, the knee brace 10, or any orthotic according to the invention, comprises a support structure 2 and various components that adjust compressive force on a body part in response to changes in atmospheric pressure. In FIG. 4, these various components are generally illustrated as a compression device 5 and means for controlling the compression device 1.

Figure 1:
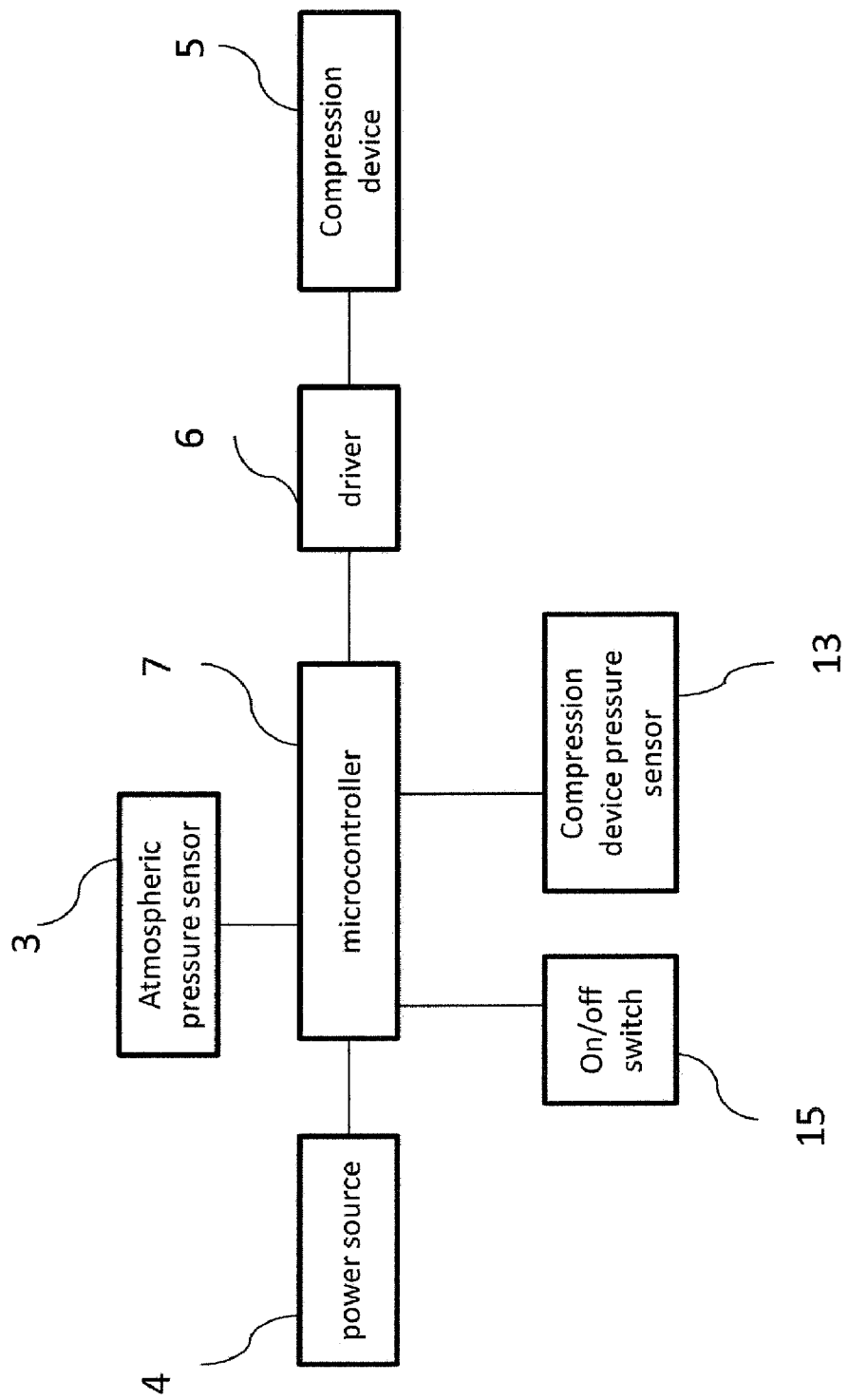
FIG. 1 is a schematic of control components utilized in the practice of the invention.

FIG. 1 provides a schematic representation of the basic components which comprise a means for controlling a compression device 1. The components include an atmospheric pressure sensor 3, a power source 4, a compression device 5, a driver 6 for the compression device 5, and a microcontroller 7 to coordinate the action of each. Other components include a compression device pressure sensor 13 to monitor the pressure exerted by or within the compression device 5. The compression device pressure sensor 13 is connected to the microcontroller 7 and can be set to control the function of the driver 6 or any of the other components. For example, the microcontroller 7 may be programmed to terminate power to the driver 6 should the compression device pressure sensor 13 record a pressure that exceeds a predetermined maximum value. Additional components include an on/off switch 15 to control power provided by the power source 4.

The components illustrated in FIG. 1 are placed proximate a body part, preferably by means of attachment to a support structure 2 which is in turn placed proximate a body part. Suitable support structures 2 include any type of support structure currently used in the manufacture of orthotics. For example, the term support structure 2, as used herein, includes compressive sleeves, wrap-around braces, or any other type of fabric or rigid structure capable of maintaining a compression device 5 proximate to or in contact with a body part. Those skilled in the art can readily incorporate the apparatus according to the invention into existing support structures 2 used in existing orthotics.

Returning to FIG. 1, the atmospheric pressure sensor 3 utilized in the practice of the invention may be any commercially available sensor suitable for incorporation into an orthotic. The primary factors one skilled in the art will consider in choosing the appropriate sensor is size, cost, and power consumption.

Representative atmospheric pressure sensors 3 suitable for use in the practice of the invention include those commercially available from EPCOS and BOSCH. The ASB1200V and T5300 pressure sensors from EPCOS and the BMP085 sensor from BOSCH are representative. It is anticipated that other, more efficient, cost effective sensors will come to the market and that those skilled in the art will be able to adjust this component of the invention to meet their particular needs. Similarly, those skilled in the art can choose the most effective commercially available microcontroller to use in the practice of the invention.

The compression device 5 utilized in the practice of the invention may be any device capable of asserting an adjustable compressive force on a body part. In preferred embodiments of the invention the compression device 5 is an air bladder 9 (FIG. 3) into which air may be selectively pumped, stored, and released.

The compression device 5 is responsive to the atmospheric pressure sensor 3 in that it may increase the compressive force exerted on a body part when the atmospheric pressure sensor 3 determines that the atmospheric pressure is below a predetermined value. It is envisioned that the predetermined value is the atmospheric pressure at which a user typically experiences increased discomfort or pain in the joint or body part at issue.

Figure 3:
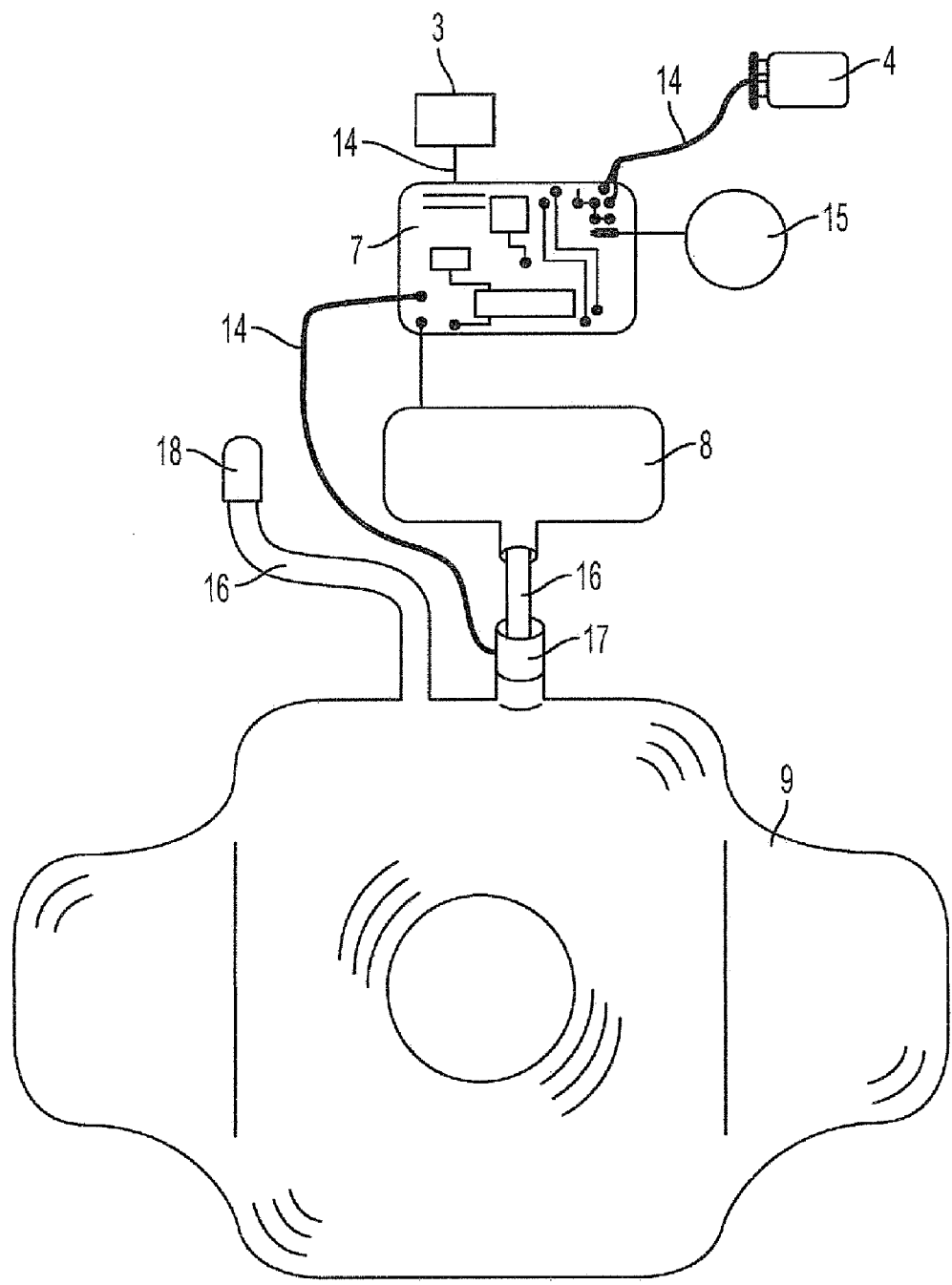
FIG. 3 illustrates a representative pneumatic system utilized in the practice of the invention.

A driver 6 accompanies the compression device 5. The driver 6 is the means of actuating the compression device 5 to exert an increased compressive force on the body part. In most instances the driver 6 is a motor of some type. A preferred embodiment of the invention utilizes an air pump 8 (FIG. 3) as a driver 6 for an inflatable air bladder 9 (FIG. 3). Air pumps suitable for use in the invention are commercially available such as the AP-2P02 micro-air pump from SmartProducts.

As noted above and in FIG. 1, the apparatus according to the invention incorporates a power source 4 and a microcontroller 7. The power source 4 powers the atmospheric pressure sensor 3, the microcontroller 7, the driver 6, and any other optional components. The exact power source 4 utilized in the practice of the invention is variable and may be one of many that are commercially available. In most instances, the power source 4 will be a compact battery of sufficient size to provide the power necessary to operate whatever sensor, microcontroller, and driver are utilized in the practice of the invention. Those skilled in the art are fully capable of identifying and connecting the appropriate power source 4 to the components of the system that require power.

It is also envisioned that a plurality of compression devices 5 may be utilized in the practice of the invention. For example, a knee orthotic according to the invention may incorporate two air bladders 9 with one on either side of the knee.

Turning now to FIG. 3, a specific embodiment of the invention is described using the knee brace as a representative orthotic. However, it is understood that the invention encompasses other orthotics shaped to support other human joints, including but not limited to wrists, elbows, shoulders, hips, and ankles.

FIG. 3 illustrates components that provide the compressive functions of the orthotic according to the invention. An inflatable air bladder 9 is provided which serves as a compression device 5. The circle in the middle of the air bladder 9 represents a hole through which a knee cap my protrude. A microcontroller 7 and an air pump 8 are provided. A power source 4, such as a battery, is connected to the microcontroller 7 by standard electrical connection means 14 appropriate for the power supply 4, microcontroller 7, and any other components. The microcontroller 7 serves to coordinate the action of the powered components. A commercially available on/off switch 15 is also connected to the microcontroller 7 by standard and appropriate electrical means 14 to control the flow of power from the power source to other components.

The atmospheric pressure sensor 3 is connected to the microcontroller 7 and power circuit by standard and appropriate electrical means 14 and measures atmospheric pressure at predetermined intervals. The air pump 8 generates air and serves as the driver 6 for the inflatable air bladder 9. The air travels through tubing 16 to the air bladder 9. The air pump 8, tubing 16, and air bladder 9 are connected to one another in a manner to provide air tight fluid communication between the components.

There is a pressure sensor 17 which measures the amount of pressure inside the air bladder 9. The air bladder pressure sensor 17 is also connected to the microcontroller 7 through appropriate connection means 14. A pressure release valve 18 is connected to the air bladder 9 by tubing 16. The air pressure release valve 18 may be any of several commercially available release valves. The air pressure relief valve 18 should be set to activate at a pressure less than the rupture pressure of the air bladder 9 or any other pressure designated by the user.

The components in FIG. 3 are then incorporated into an orthotic such as the knee brace shown in FIG. 4 where the air bladder 9 serves as the compression device 5 and the other components of FIG. 3 serve as the means for controlling the compression device 1.

The invention also encompasses a method of providing support to a body part. In broad terms, the method according to the invention comprises the steps of exerting a compressive force on a body part and altering the compressive force exerted on the body part based upon changes in the atmospheric pressure.

In most instances, the step of exerting a compressive force on a body part comprises placing an orthotic incorporating the basic components of the apparatus according to the invention proximate a body part. The method continues by monitoring the atmospheric pressure. If the atmospheric pressure falls below a predetermined value, the compressive force exerted by the compression device may increase.

Figure 2:
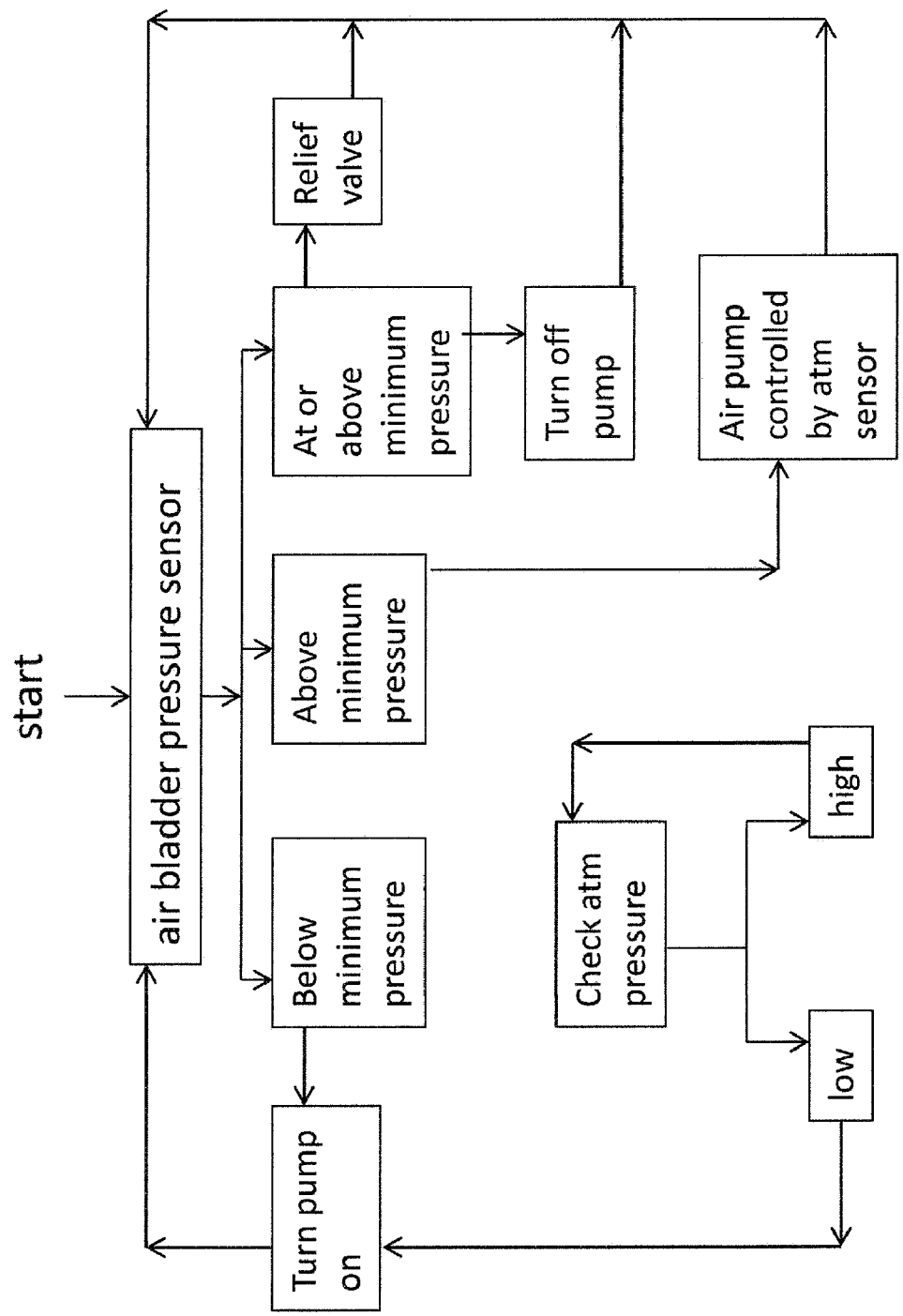
FIG. 2 is a flow chart of a logic circuit utilized in the practice of the invention.

FIG. 2 illustrates the logic circuit utilized in the practice of the method according to the invention. This logic circuit is characterized utilizing the air bladder embodiment discussed earlier for ease of understanding. The method comprises positioning an air bladder 9 proximate a body part to exert a compressive force on the body part. The method continues by placing an initial quantity of air with the air bladder. The quantity of air initially placed within the bladder should be sufficient to meet a minimum level of pressure within the bladder; the minimum level being determined by the user with input from a health care professional. It is envisioned that the use of a minimum level of air pressure within the bladder is necessary to compensate for long term, slow loss of air pressure due to normal wear and tear that is unrelated to changes in atmospheric pressure.

Once the minimum level of air pressure within the air bladder is attained the pressure within the air bladder is monitored using an air bladder pressure sensor 17 as described above. There are three possible outcomes of this measurement.

First, if the air pressure within the air bladder 9 is at or above a predetermined maximum pressure, the microcontroller 7 will terminate the action of the driver 6 (e.g., the air pump 8) if the driver is operating. Alternatively and/or concurrently with this action, a pressure release valve 18 may activate to reduce pressure within the air bladder.

Second, if the air pressure within the air bladder is below a set minimum pressure, the air bladder pressure sensor 17 signals the microcontroller 7 to turn on the air pump 8 and it remains on until the pressure in the air bladder reaches the set minimum pressure.

Third, once the minimum air bladder pressure is reached, the signal from the air bladder pressure sensor will no longer actuate the air pump 8 and the air pump 8 is controlled by the atmospheric pressure sensor 3.

Concurrently with the steps of monitoring the air bladder pressure, the atmospheric pressure is also monitored. If the atmospheric pressure is below a predetermined value then the driver 6 of the compression device 5 (e.g., the air pump 8 of the air bladder 9) is actuated and the air bladder pressure is monitored. Additional air is supplied to the air bladder 9 until the set maximum pressure is reached. Once the air bladder pressure reaches the set maximum value the air pump 8 is turned off and the monitoring loops continue. If the atmospheric pressure is above a predetermined value then the atmospheric pressure sensor does not actuate the air pump and the monitoring loops continue.

In summary, there are two monitoring loops that occur simultaneously during the practice of the invention. The atmospheric pressure is monitored continuously along with the pressure inside the air bladder 9. Both the atmospheric pressure sensor 3 and the air bladder pressure sensor 17 may independently actuate the air pump 8. The air bladder pressure sensor 17 keeps the air bladder pressure above a minimum value to be determined by a user and it acts as a safety switch to prevent over inflation of the air bladder 9. The atmospheric pressure sensor 3 adjusts the air bladder pressure within the range defined by the minimum allowed pressure and the maximum allowed pressure.

As will be apparent to those skilled in the art, various changes and modifications may be made to the method and apparatus of the present invention without departing from the spirit and scope of the invention as determined in the appended claims and their legal equivalent.

In the drawings and specification, there have been disclosed typical embodiments on the invention and, although specific terms have been employed, they have been used in a generic and descriptive sense only and not for purposes of limitation, the scope of the invention being set forth in the following claims.

The invention claimed is:

1. An orthotic that monitors atmospheric pressure and increases compressive force exerted by an inflatable air bladder on a body part when the atmospheric pressure falls below a predetermined pressure.

2. An orthotic according to claim 1 comprising:
an atmospheric pressure sensor;
an inflatable air bladder that is responsive to said atmospheric pressure sensor and increases the level of compression applied to a body part when the atmospheric pressure falls below a predetermined pressure;
a power source for supplying power to said atmospheric pressure sensor; and
a pump for supplying air to said air bladder.

3. An orthotic according to claim 2 further comprising:
a microprocessor to coordinate the action of said atmospheric pressure sensor and said pump.

4. An orthotic according to claim 2 further comprising a plurality of inflatable air bladders.

5. An orthotic comprising:
an inflatable air bladder;
a support structure for said inflatable air bladder, said support structure capable of maintaining said air bladder proximate a body part;
an atmospheric pressure sensor;
a pump for supplying air to said inflatable air bladder, said pump being responsive to said atmospheric pressure sensor; and
a power source for supplying power to said atmospheric pressure sensor and said pump.

6. An orthotic according to claim 5 further comprising:
a relief valve for relieving pressure in said air bladder; and
a microprocessor to coordinate the action of said power source, said atmospheric pressure sensor, and said pump.

7. An orthotic according to claim 6 further comprising an air bladder pressure sensor.

8. An orthotic according to claim 5 wherein said support structure is shaped to support a human joint.

9. An orthotic according to claim 8 wherein said joint is selected from the group consisting of a wrist, an elbow, a shoulder, a hip, a knee, and an ankle.

10. An orthotic according to claim 5 having a plurality of air bladders.

11. A method of providing support to a body part, the method comprising the steps of:
exerting a compressive force on the body part via an inflatable air bladder, and
altering the compressive force exerted by the inflatable air bladder on the body part based upon changes in atmospheric pressure.

12. A method according to claim 11 wherein:
the step of exerting a compressive force on the body part comprises placing an orthotic proximate the body part, wherein the orthotic incorporates the inflatable air bladder.

13. A method according to claim 11 wherein the step of altering the compressive force comprises monitoring atmospheric pressure and increasing the compressive force exerted on the body part if atmospheric pressure is below a predetermined pressure.

14. A method according to claim 11 wherein the step of exerting a compressive force comprises:
positioning an inflatable air bladder proximate a body part; and
inflating the air bladder to exert a compressive force on the body part.

15. A method according to claim 14 wherein the step of altering the compressive force comprises:
monitoring the air pressure within the air bladder;
monitoring atmospheric pressure; and
supplying additional air to the air bladder if the atmospheric pressure is below a predetermined pressure.

16. A method according to claim 15 wherein the step of monitoring atmospheric pressure comprises connecting an atmospheric pressure sensor to a microcontroller and a power source.

17. A method according to claim 15 wherein the step of supplying additional air to the air bladder comprises connecting a pump to the air bladder and to a microprocessor, power source, and atmospheric pressure sensor where the pump is responsive to the atmospheric pressure sensor.

* * * * *